United States Patent [19]

Pretlow, III

[11] Patent Number: 5,433,207

[45] Date of Patent: Jul. 18, 1995

[54] METHOD AND APPARATUS TO CHARACTERIZE ULTRASONICALLY REFLECTIVE CONTRAST AGENTS

[76] Inventor: Robert A. Pretlow, III, 301 Birkdale, Yorktown, Va. 23693

[21] Appl. No.: 153,930

[22] Filed: Nov. 15, 1993

[51] Int. Cl.⁶ .............................................. A61B 8/00
[52] U.S. Cl. ................................................ 128/662.02
[58] Field of Search .............. 128/662.02, 672; 424/9, 424/450, 2; 73/627, 646, 861.25

[56] References Cited

U.S. PATENT DOCUMENTS

| | | | |
|---|---|---|---|
| 5,215,680 | 6/1993 | D'Arrigo | 252/307 |
| 5,230,882 | 7/1993 | Unger | 424/9 |
| 5,255,683 | 10/1993 | Monaghan | 128/662.02 |

Primary Examiner—George Manuel

[57] ABSTRACT

A method and apparatus for characterizing the time and frequency response of an ultrasonically reflective contrast agent is disclosed. An ultrasonically reflective contrast agent is injected, under constant pressure, into a fluid flowing through a pump flow circuit. The fluid and the ultrasonically reflective contrast agent are uniformly mixed in a mixing chamber, and the uniform mixture is passed through a contrast agent chamber. The contrast agent chamber is acoustically and axially interposed between an ultrasonic transducer chamber and an acoustic isolation chamber. A pulse of ultrasonic energy is transmitted into the contrast agent chamber from the ultrasonic transducer chamber. An echo waveform is received from the ultrasonically reflective contrast agent, and it is analyzed to determine the time and frequency response of the ultrasonically reflective contrast agent.

20 Claims, 12 Drawing Sheets

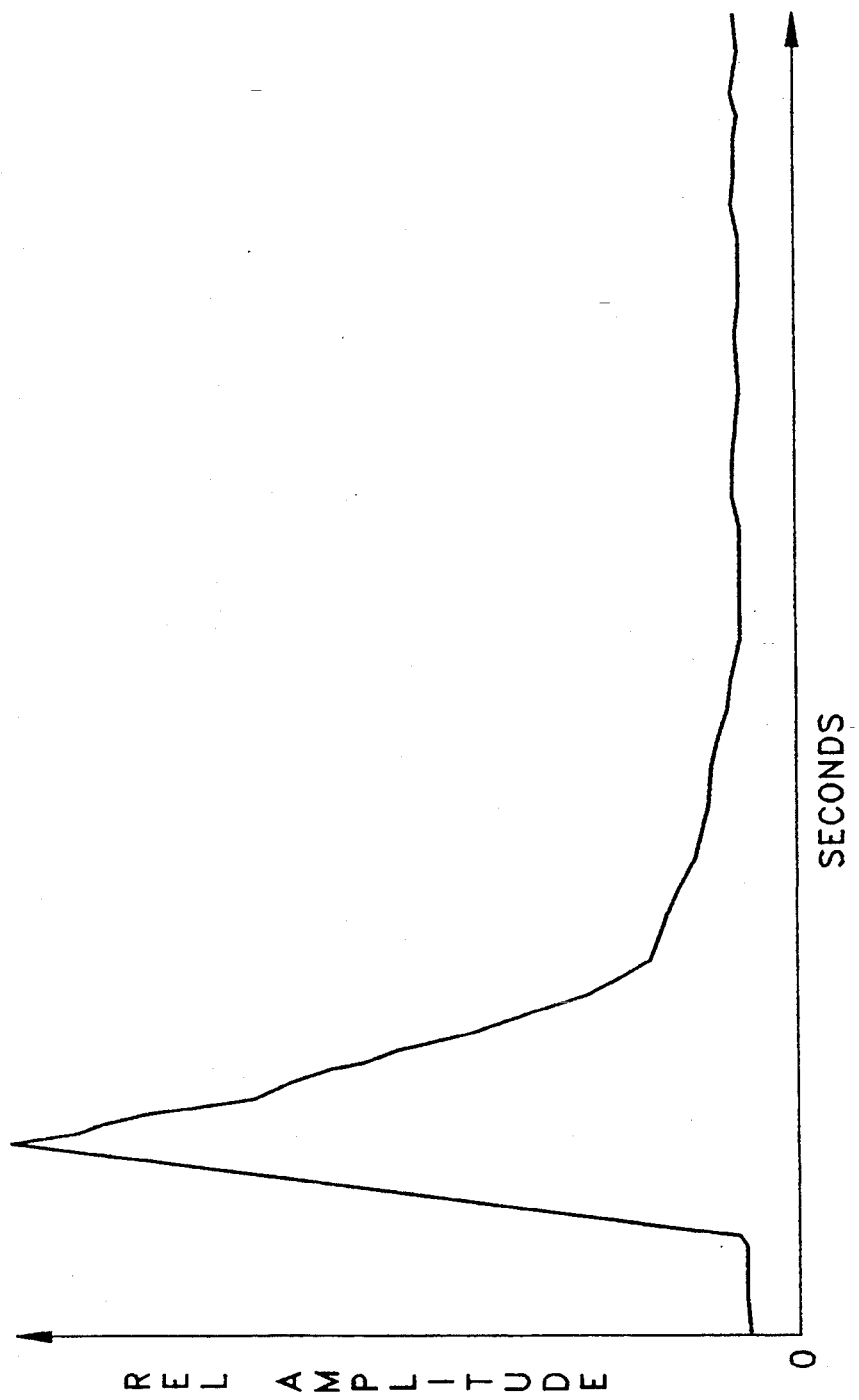

METHOD AND APPARATUS TO CHARACTERIZE ULTRASONICALLY REFLECTIVE CONTRAST AGENTS

ORIGIN OF THE INVENTION

The invention described herein was made in the performance of work under a NASA contract and is subject to the provisions of Section 305 of the National Aeronautics and Space Act of 1958, as amended, Public Law 85-568 (72 Stat. 435 42 U.S.C. 2457).

BACKGROUND

One method of medical ultrasonic imaging involves the use of ultrasonically reflective contrast agents. Such contrast agents enhance the image obtained in clinical studies by increasing the contrast of and by outlining the anatomic structures being studied, e.g., the heart (its chambers, blood vessels, and tissue). Examples of commercially available ultrasonically reflective contrast agents include, "ALBUNEX" brand ultrasonically reflective contrast agent manufactured by Molecular Biosystems, San Diego, Calif., and "ECHOVIST" brand ultrasonically reflective contrast agent manufactured by Schering Corporation, Germany.

New contrast agents should be studied in the laboratory to characterize their time and frequency responses to ultrasonic energy before they are used with patients. An analysis system is therefore needed in order to characterize the time and frequency responses of particular ultrasonically reflective contrast agents, and so that one ultrasonically reflective contrast agent may be compared with another ultrasonically reflective contrast agent.

SUMMARY

The present invention is directed to a method and an apparatus that satisfies the need for an analysis system for characterizing the time and frequency response of ultrasonically reflective contrast agents. A method of characterizing the time and frequency response of an ultrasonically reflective contrast agent having the features of the present invention includes the steps of injecting, under constant pressure, the ultrasonically reflective contrast agent into a fluid stream. The fluid stream is passed through a mixing chamber so as to uniformly mix the ultrasonically reflective contrast agent and the fluid flowing in the fluid stream. The uniform mixture of the ultrasonically reflective contrast agent and the fluid is passed through a contrast agent chamber, and a pulse of ultrasonic energy is transmitted into the contrast agent chamber. An echo waveform is received from the ultrasonically reflective contrast agent, and it is analyzed to determine the time and frequency response of the ultrasonically reflective contrast agent.

Another method of characterizing the time and frequency response of an ultrasonically reflective contrast agent having the features of the present invention includes the step of injecting, under constant pressure, an ultrasonically reflective contrast agent into a fluid flowing through a pump flow circuit. The fluid is passed through a mixing chamber so as to uniformly mix the ultrasonically reflective contrast agent and the fluid. The uniform mixture of the ultrasonically reflective contrast agent and the fluid is passed through a contrast agent chamber that is acoustically interposed between an acoustic isolation chamber and an ultrasonic transducer chamber. A pulse of ultrasonic energy is transmitted into the contrast agent chamber from the ultrasonic transducer chamber. An echo waveform is received from the ultrasonically reflective contrast agent, and it is analyzed to determine the time and frequency response of the ultrasonically reflective contrast agent.

An apparatus for analyzing an ultrasonically reflective contrast agent having the features of the present invention comprises a fluid that is pumped through a pump flow circuit, and an injector filled with the ultrasonically reflective contrast agent for injecting the ultrasonically reflective contrast agent into the fluid under constant pressure. The mixture of the injected ultrasonically reflective contrast agent and the fluid is uniformly mixed in a mixing chamber and then passed into a contrast agent chamber. A pulse of ultrasonic energy is transmitted by an ultrasonic transducer into the contrast agent chamber, and the echo waveform from the ultrasonically reflective contrast agent is received by the ultrasonic transducer for analysis to determine the time and frequency characteristics of the ultrasonically reflective contrast agent.

The present invention is also directed toward a method of analyzing an ultrasonic echo waveform received from an ultrasonically reflective contrast agent. The method includes the steps of digitizing the echo waveform into discrete data points, and computing mean amplitude data points from the discrete data points. Spurious mean amplitude data points are corrected, and the mean amplitude data points are smoothed. The mean amplitude data points are plotted against time, and parameter calculations are performed on the plot of the mean amplitude data points against time curve.

DRAWINGS

For a more complete understanding of the present invention reference should be made to the description, which is set forth below. This description should be read together with the accompanying drawings, wherein:

FIG. 1 is a schematic diagram of the present invention.

FIGS. 2a and 2b comprise a two-part diagram of typical ultrasonic waveforms transmitted and received by the ultrasonic transducer.

FIG. 12 is a typical mean amplitude data points against time curve.

DESCRIPTION

Figure 1:
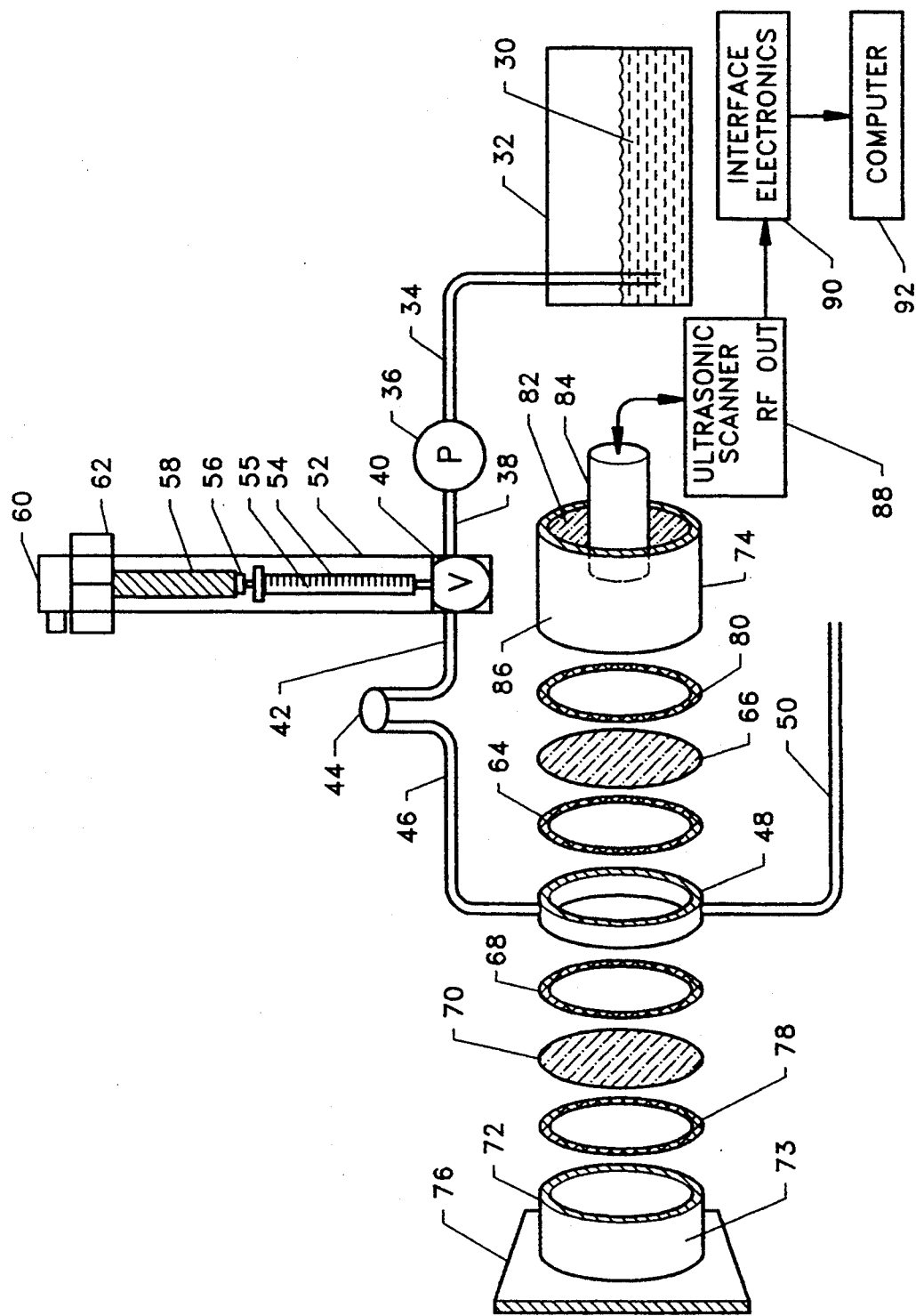

FIG. 1 illustrates the present invention. A fluid 30 contained within a reservoir 32 is pumped through a pump flow circuit. The pump flow circuit comprises a pipe 34, a pump 36, a pipe 38, a three-way valve 40, a pipe 42, a mixing chamber 44, a pipe 46, a contrast agent chamber 48, and a pipe 50 which serves as the pump flow circuit discharge. The fluid 30 preferably is either distilled water or saline solution, but it may comprise any fluid which is suitable for mixing with an ultrasonically reflective contrast agent. The pump 36 preferably is a variable speed pump. Such a pump will allow the flow parameters of the present invention to be varied in order to determine the result and effects on the echo waveform. Such information can be extra-polated to clinical situations.

Referring again to FIG. 1, a tube 52 is attached to the valve 40. A syringe 54 having a plunger 56 is within the tube 52. The syringe 54 is connected to the three-way valve 40. The three-way valve 40 prevents backfilling of the syringe 54 with the fluid 30. The syringe 54 is filled with an ultrasonically reflective contrast agent 55 to be analyzed by the present invention. A weight 58 is placed above the plunger 56 and is held in place by a trigger release mechanism 60. The trigger release mechanism 60 may comprise any device known in the art such as removable pin placed through both the tube 52 and the 58, or an electromechanical device controllable by a computer 92. The level of the weight 58 compared to the plunger 56 may be adjusted by a weight level adjust 62. The weight level adjust 62 may comprise any device known in the art such as a friction collar or a releasable screw thread. The purpose of the weight level adjust is to allow the positioning of the weight 58 so that it is just above the plunger 56. This prevents the microspheres comprising the ultrasonic contrast agent 55 from being damaged from a sudden impulse caused by the weight 56 from striking the plunger 56.

The ultrasonically reflective contrast agent 55 is caused to be injected into the fluid 30, under constant pressure, at the three-way valve 40 when the trigger release mechanism 60 is released because the weight 58 presses down upon the plunger with a constant force. The constant pressure, in addition to preventing the destruction of the ultrasonically reflective contrast agent 55, eliminates the variability of injection rate inherent with manual injection. The weight 58, the trigger release mechanism 60, and the weight level adjust 62 may all be replaced with a mechanical or an electro-mechanical actuator.

The fluid 30 and the ultrasonically reflective contrast agent 55 flow out of the three-way valve 40, through the pipe 42, and into a mixing chamber 44. The mixing chamber 44 is cylindrical in shape. Its purpose is to create a rotational flow having minimal turbulence to promote uniform mixing of the fluid 30 and the ultrasonically reflective contrast agent 55.

The uniform mixture of the fluid 30 and the ultrasonically reflective contrast agent 55 exit the mixing chamber 44 through the pipe 46 and enter the contrast agent chamber 48. The contrast agent chamber 48 is cylindrical in shape to prevent turbulence in the fluid flow. The volume of the contrast agent chamber 48 may be varied by changing its size. The contrast agent chamber 48 is sealed on one side by a gasket 64 and a membrane seal 66, and on the other side by a gasket 68 and a membrane seal 70. The gaskets 64 and 68 may be comprised of any suitable material such as rubber, and the membrane seals 66 and 70 may also comprise any suitable material such as vinyl food wrap.

The contrast agent chamber 48 is acoustically interposed and axially aligned between two additional cylindrical chambers, an acoustic isolation chamber 72 and an ultrasonic transducer chamber 74. The acoustic isolation chamber 72 has the same diameter as the contrast agent chamber 48. One side of the acoustic isolation chamber is sealed with a plate 76, while the other side is sealed with a gasket 78 and with the membrane seal 70. The acoustic isolation chamber 72 is filled with a liquid 73 which may preferably be water or saline solution. The purpose of the acoustic isolation chamber 72 is to acoustically isolate the contrast agent chamber 48 so that the ultrasonic signal properties of the ultrasonically reflective contrast agent 55 may be studied.

The ultrasonic transducer chamber 74 has the same diameter as the contrast agent chamber 48. One side of the ultrasonic transducer chamber 74 is sealed with a gasket 80 and with membrane seal 66. The other side of the ultrasonic transducer chamber 74 is sealed with a seal 82. An ultrasonic transducer 84 is mounted at the center point of the seal 82. The gaskets 78 and 80 may be comprised of any suitable material, such as rubber, while the seal 82 can be any suitable material strong enough to support the ultrasonic transducer 84. The ultrasonic transducer chamber 74 is filled with a liquid 86 which may preferably be water or saline solution.

A conventional medical ultrasonic echocardiography scanner 88 supplies radio frequency energy to the ultrasonic transducer 84 and receives a radio frequency echo waveform back from the ultrasonic transducer 84. Medical ultrasonic echocardiography scanners such as those manufactured by General Electric Medical Systems, Milwaukee, Wis., and by Advanced Technology Laboratories, Bothell, Wash., may be used in the present invention.

The ultrasonic echocardiography scanner 88 produces a radio frequency output corresponding to the radio frequency echo waveform from the ultrasonic transducer 84. It is fed to an interface electronics module 90 which digitizes the echo waveform into discrete data points. A LeCroy Model No. 9450A oscilloscope, manufactured by LeCroy Company, Chestnut Ridge, N.Y., may be utilized to digitize the echo waveform. The digitized waveform is then fed to the computer 92, which may, for example, be a Compaq 486, for analysis and computation of the parameters of the waveform.

Figure 2A:
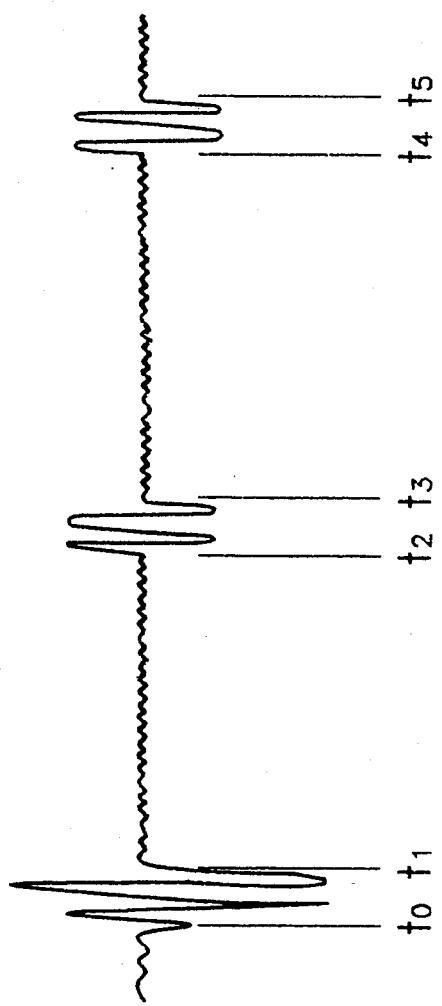
Figure 2B:
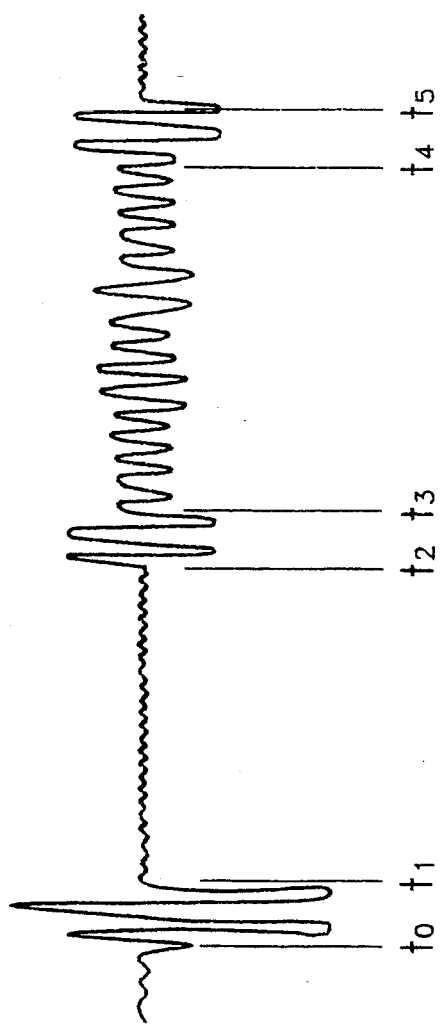

FIG. 2a illustrates a typical waveform of a pulse of ultrasonic energy from the ultrasonic transducer 84. The; pulse of energy starts at time t and continues until time t. With no ultrasonically reflective contrast agent present in the contrast agent chamber 48, the only reflections or echos received by the ultrasonic transducer 84 are those from the membrane seal 66, represented by a typical waveform beginning at time t and continuing until time t, and from membrane seal 70, represented by a typical waveform beginning at time t and continuing until time t. FIG. 2b is identical to FIG. 2a, except that it shows a typical echo waveform of the ultrasonically reflective contrast agent 55 when it is present in the contrast agent chamber 48. This waveform begins at time t and continues until time t.

Figure 3:
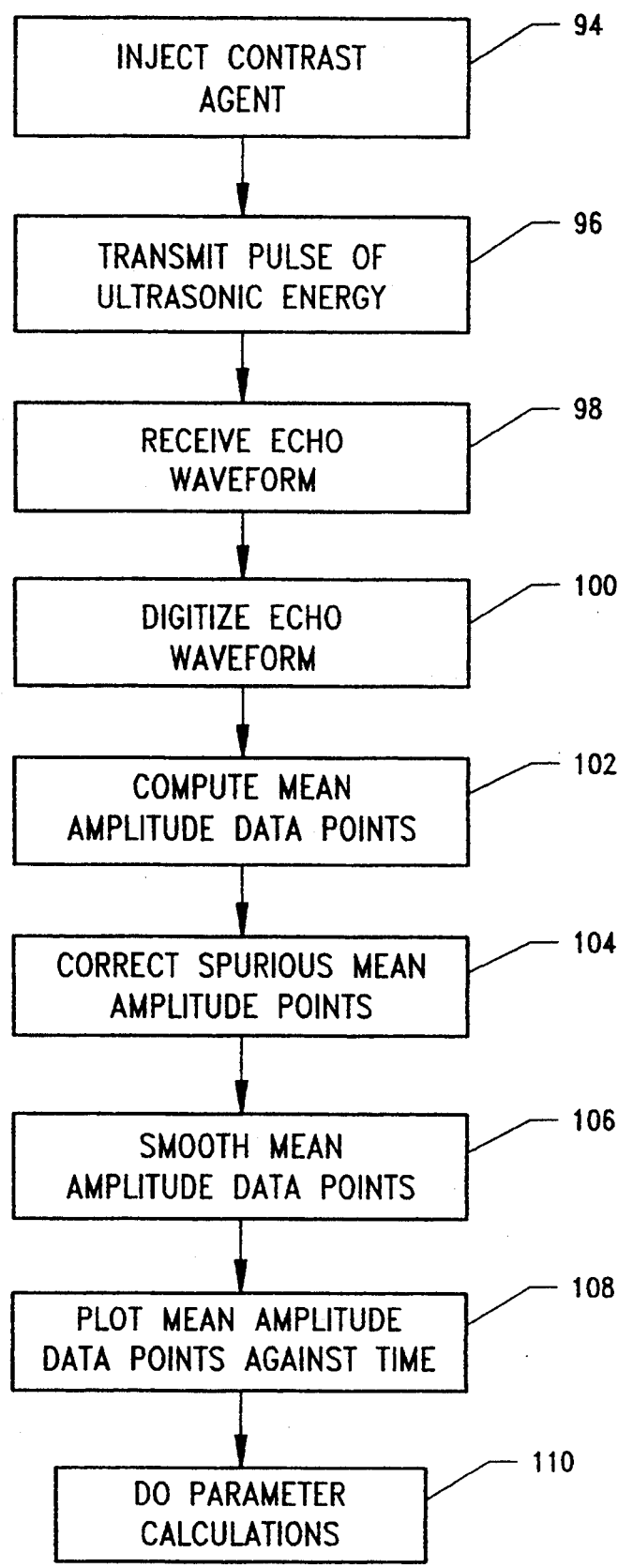
FIG. 3 is an overview flow diagram of the method of analyzing the echo waveform.

FIG. 3 is an overview flow diagram of the steps of analyzing the echo waveform. As depicted in block 94, the ultrasonically reflective contrast agent 55 is injected into the fluid 30 flowing through the pump flow circuit. The ultrasonically reflective contrast agent 55, once injected, passes through the contrast agent chamber 48. As the ultrasonically reflective contrast agent 55 passes through the contrast agent chamber 48, the ultrasonic transducer 84 transmits a pulse ultrasonic energy, as depicted by block 96, and receives the echo waveform as depicted by block 98. The echo waveform is then digitized into discrete data points, as depicted by block 100, and mean amplitude data points are computed by the computer 92 from the discrete data points, as illustrated in block 102. The mean amplitude data points are processed by the computer 92 to correct spurious mean amplitude data points, as depicted by block 104, and the mean amplitude data points are then smoothed, again by the computer 92, as illustrated by block 106. The next step is to plot the mean amplitude data points against time as shown by block 108, and to use the computer 92 to perform parameter calculations on the plot of the mean amplitude data points against time curve, as depicted by block 110. The parameter calculations are performed on the smoothed mean amplitude data points stored in the computer 92.

Figure 4:
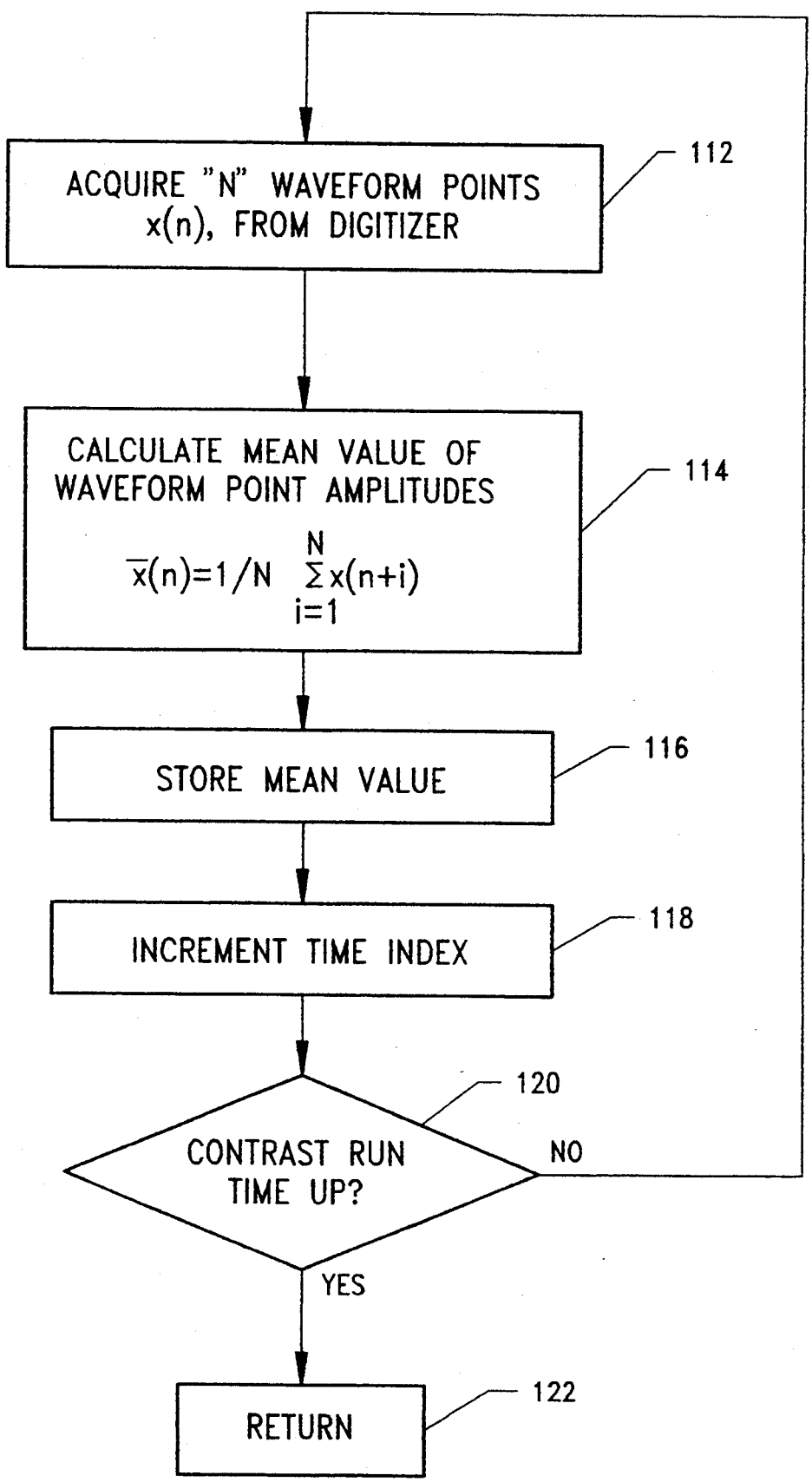
FIG. 4 is a flow diagram of the routine for computing the mean amplitude data points from the discrete data points.

FIG. 4 is a flow diagram of the routine utilized by the present invention to compute the mean amplitude data points from the discrete data points. The first step in this routine is to acquire "N" discrete data points which represent the echo waveform X(n), from the digitizer, or interference electronics module 90, as depicted by block 112. The absolute value of the discrete data points is averaged, as depicted in block 114, to obtain a mean amplitude data point, and the mean amplitude data point is stored, as illustrated by block 116, under a time index address. After a prescribed time delay, the time increment address is incremented, as illustrated by block 118, and a decision is made to repeat the sequence, as depicted by decision block 120, based on whether or not any ultrasonically reflective contrast agent 55 remains in the contrast agent chamber 48. This may be determined physically by watching the discharge from the pump flow circuit or electronically by programming the computer 92 to sense when a waveform of the type illustrated by FIG. 2a is present. If the computer 92 determines that the decision at block 120 is "YES", then the return block 122 returns the computational flow to block 104 of FIG. 3 for correction of spurious mean amplitude data points.

Figure 5:
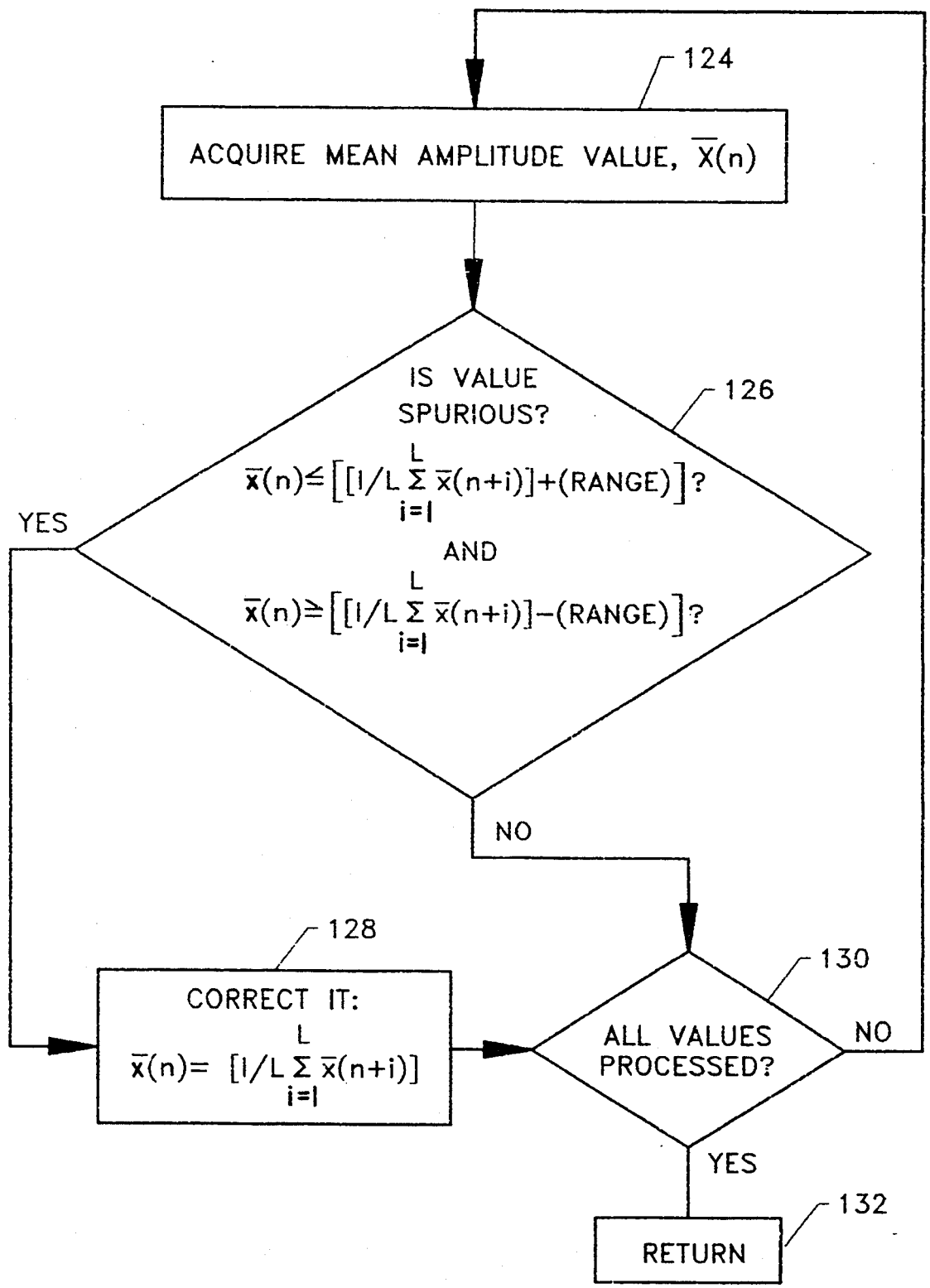
FIG. 5 is a flow diagram of the routine for computing spurious mean amplitude data points.

A flow diagram of the routine to correct spurious mean amplitude data points is illustrated in FIG. 5. This routine involves comparing each mean amplitude data point to a running average of a number of time-related points. If the given point varies too greatly from that average, then a substitution is made of the running average for that point. Referring to FIG. 5, a mean amplitude data point is acquired from the memory of the computer 92, as depicted by block 124. This data point, as depicted by decision block 126, is compared a running average of a number "L" of mean amplitude data points to determine if the data point is inside or outside of the running average plus or minus a predetermined range value. If the particular data point is outside of the running average plus or minus the predetermined range, the running average is replaced for that data point, as illustrated by block 128, and the computational flow proceeds to a decision block 130. If the particular data point is inside of the running average plus or minus the predetermined range, the computer 92 returns the computational flow to block 124, as illustrated by decision block 130. Once all of the stored values are processed, the computer 92 returns the computational flow, as illustrated by return block 132, to block 106 of FIG. 3.

Figure 6:
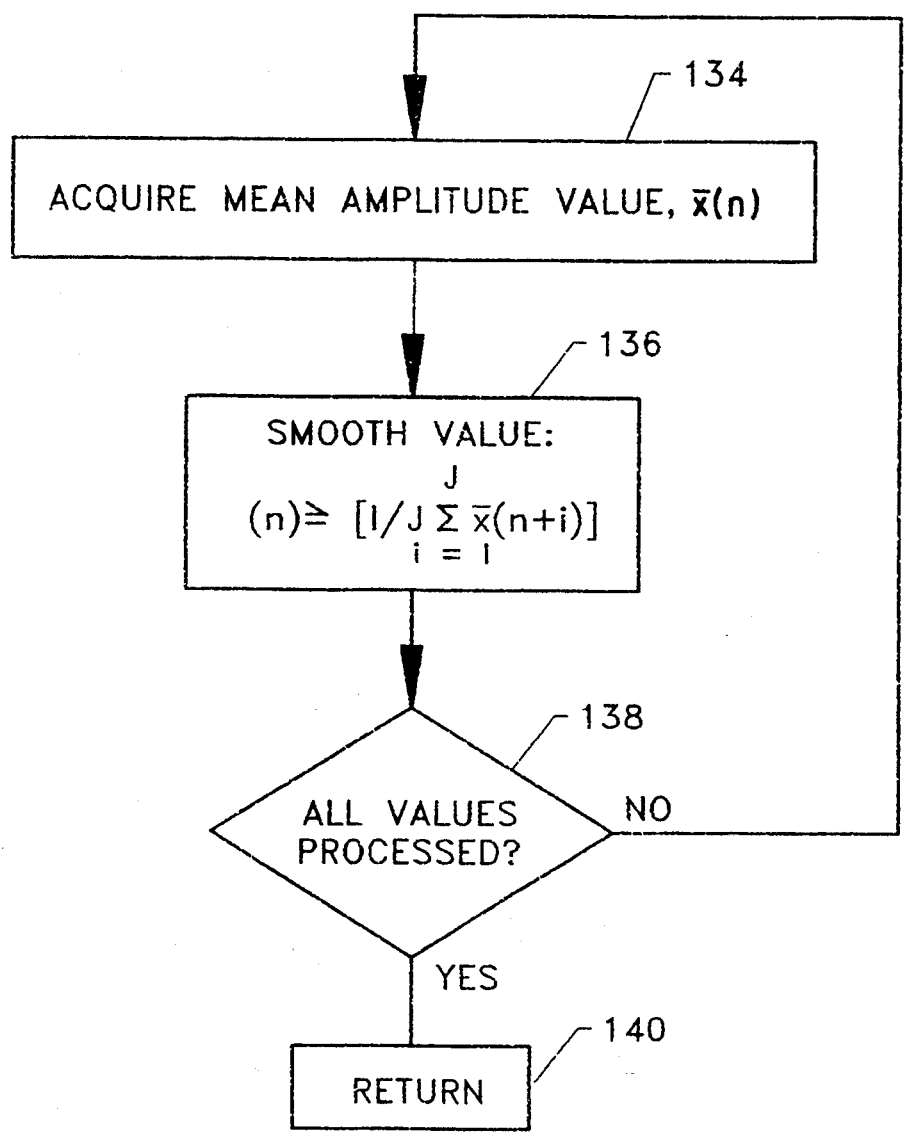
FIG. 6 is a flow diagram of the routine for smoothing the mean amplitude data points.

To smooth the mean amplitude data points, a running average of a prescribed number "J" of time related data points is substituted for each mean amplitude data point. The subroutine which performs this function is illustrated by the flow diagram illustrated in FIG. 6. A mean amplitude data point is acquired from the memory of the computer 92, as depicted by block 134. This data point is replaced by a running average of a number of mean amplitude data points, as illustrated by block 136. If all of the values have not been processed, decision block 138 returns the computational flow to block 134; and if all of the values have been processed, the computational flow is return by return block 140 to block 108 of FIG. 3.

The computer 92 is used in the present invention to calculate a variety of parameters that relate to the mean amplitude data points against time curve. These parameters include the curve peak value, time to curve peak, curve baseline, curve noise threshold, and the time interval from the start of injection to the point of noise threshold for the ascending curve and for the descending curve. Other parameters include the time interval from the point at which the curve exceeds the noise threshold to the time of the peak curve, and the time of appearance of the contrast agent in the contrast agent chamber. Additional parameters include the time from the noise threshold point to the amplitude point halfway between the noise threshold point for the curve ascending and descending, the slope of the curve at the one half peak amplitude ascending and descending points, and the area under curve.

Figure 7:
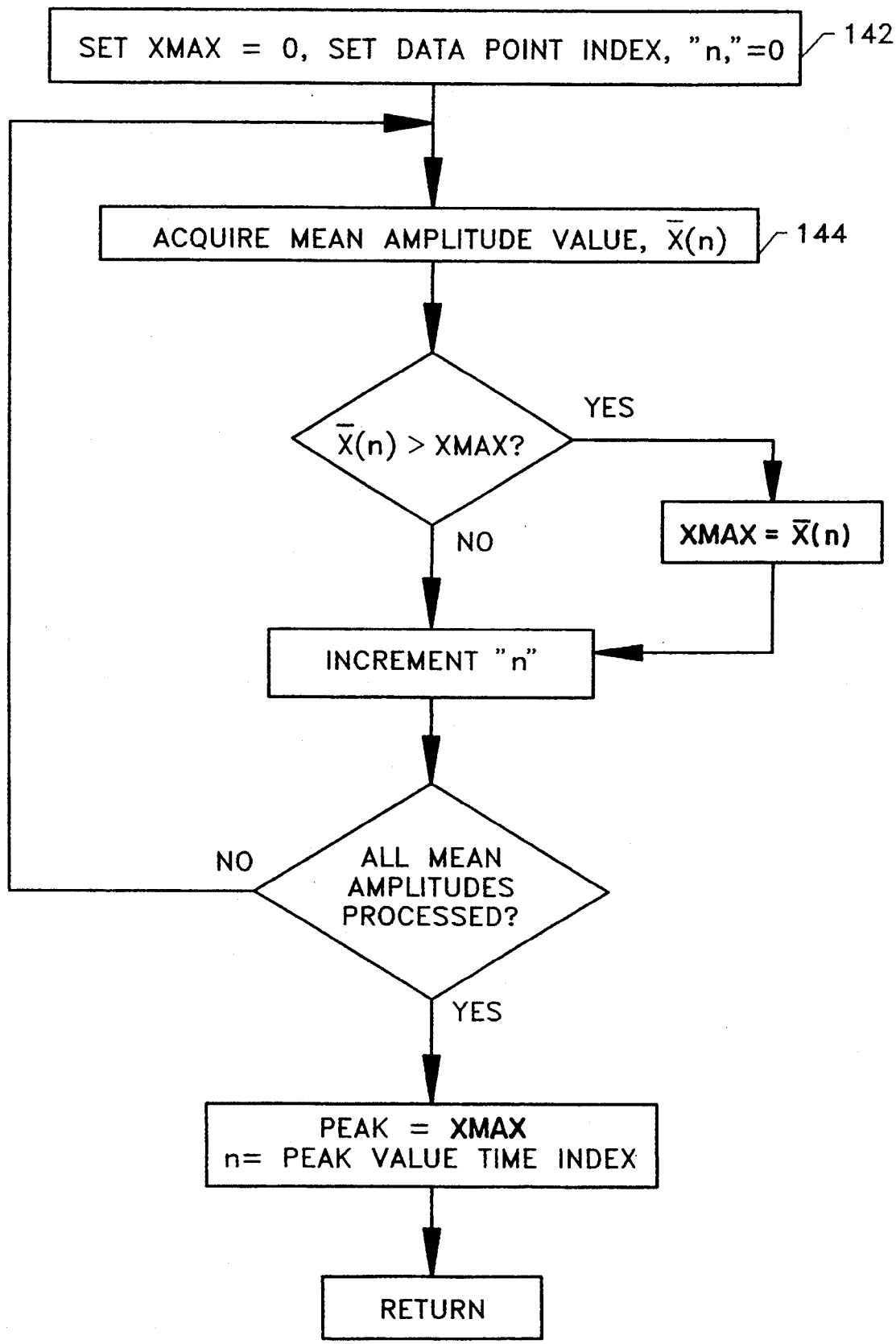
FIG. 7 is a flow diagram of the routine for calculating the curve peak value.

FIG. 7 is a flow diagram of the routine used by the computer 92 to calculate the curve peak value. The value of "XMAX" is first set to zero and a data point index, "n," is also set to zero, as illustrated by block 142. A mean amplitude data point is acquired from the memory of the computer 92, as illustrated by block 144. This value is compared, as illustrated by decision block 144 to the value of XMAX. If the value of the particular mean amplitude data point greater than XMAX, then XMAX, as illustrated by block 148, is set to the value of the mean amplitude data point and the data point index "n" is incremented as illustrated by block 150. If the value of the particular mean amplitude data point is less than XMAX, then only the data point register "n" is incremented. Processing continues until all of the mean amplitude values are processed, as illustrated by decision block 152. The next step of this routine, as represented by block 154, is to set "PEAK" equal to XMAX, and to set n to the time index of the peak value. The computer 92 then returns to block 110 of FIG. 3, as depicted by return block 156.

Figure 8:
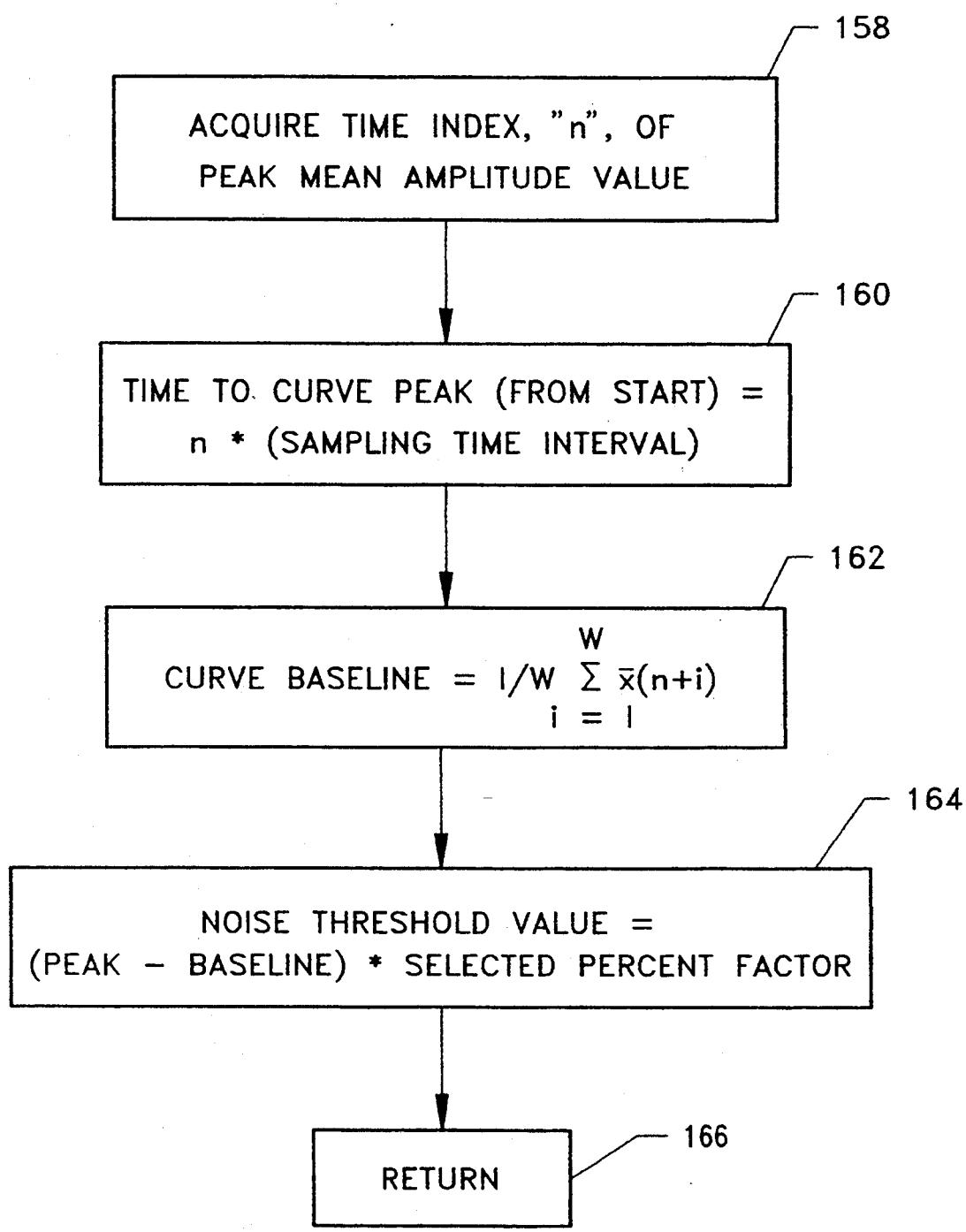
FIG. 8 is a flow diagram of the routine for calculating the time interval from the injection of the ultrasonically reflective contrast agent, the curve baseline or bias value, and the curve noise threshold.

The next routine, illustrated by FIG. 8, calculates the time interval from the injection of the ultrasonically reflective contrast agent 55 into the fluid 30, the curve baseline or bias value over a prescribed window of initial time related points that occur before injection of the ultrasonically reflective contrast agent 55, and the curve noise threshold. As illustrated by block 158 FIG. 8, the time index "n" of the peak value, determined in block 154, is acquired by the computer 92. The time to curve peak from the injection of the ultrasonically reflective contrast agent 55 is determined in block 160 by multiplying n by the sampling time interval. The curve baseline is calculated in block 162 by averaging a predetermined number "W" of time related points that occur before the injection of the ultrasonically reflective contrast agent ,55. The noise threshold value, calculated in block 164, is determined by taking the difference between the peak and baseline values and multiplying that difference by an arbitrary percent value, e.g. 10%. Thus, the mean amplitude values of the curve will have to exceed the noise threshold value before they will be considered in the computations. At the conclusion of these computations, the computer 92 then returns the computational flow to block 110 of FIG. 3, as illustrated by return block 166.

Figure 9:
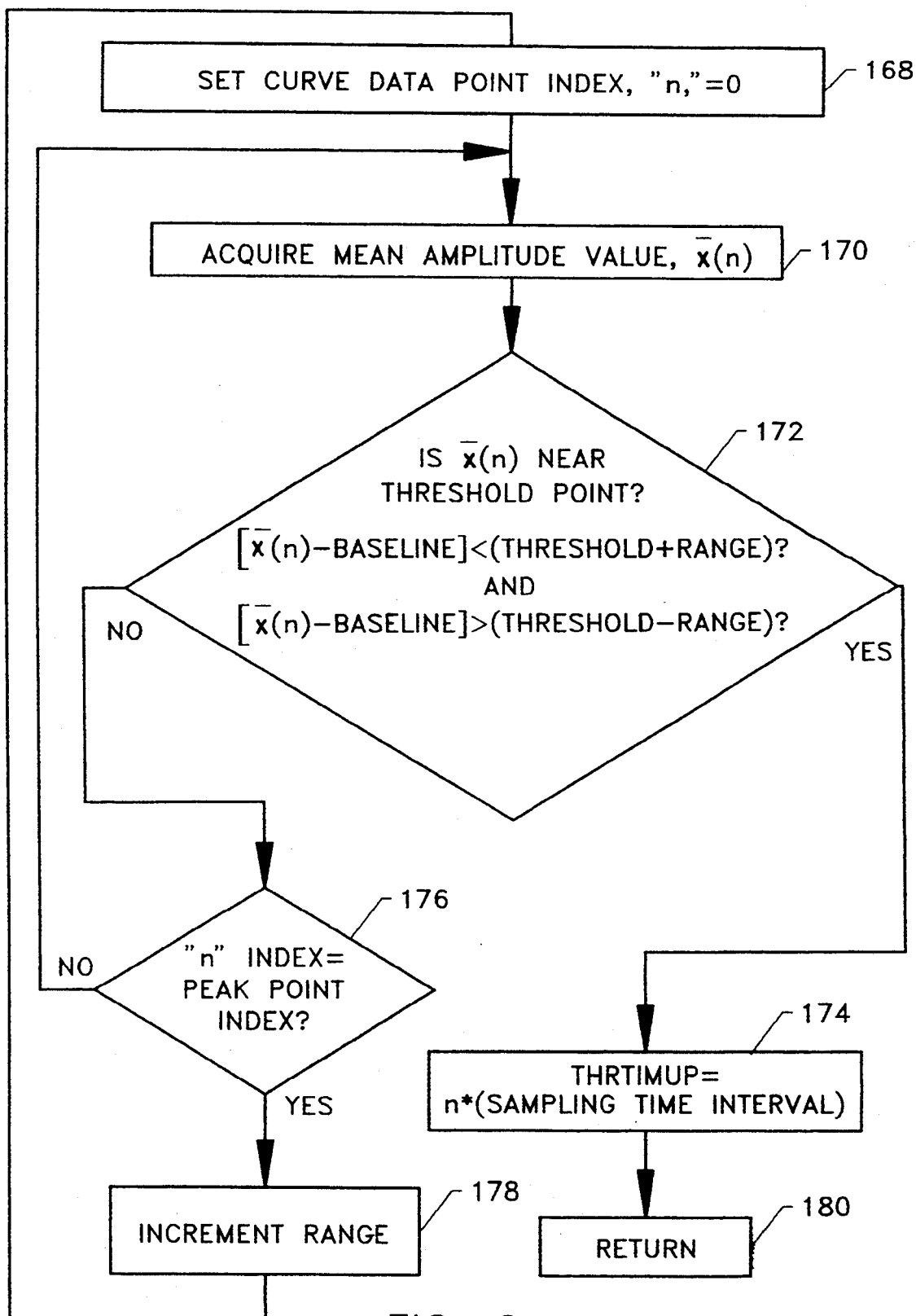
FIG. 9 is a flow diagram of the routine for calculating the time from injection of the ultrasonically reflective contrast agent to the noise threshold time point for the curve ascending.

FIG. 9 illustrates the, routine for calculating the time from the injection of the ultrasonically reflective contrast agent 55 into the fluid 30 to the noise threshold time point for the curve ascending. What is desired is the time index of the mean amplitude value closest to the noise threshold value. The routine operates by first setting the curve data point index "n" to zero, as illustrated by block 168. A mean amplitude data point is acquired from the memory of the computer 92, as illustrated by block 170, and a comparison is made in decision block 172 to determine if the mean amplitude data point is near the noise threshold point. If the noise threshold is within a range of each mean amplitude data point value plus or minus a prescribed range value, then that is the noise threshold point. To determine the actual time to the noise threshold point in seconds, the time index of the mean amplitude data point within the point range is multiplied by the sampling time interval to yield the value "THRTIMUP," as illustrated by block 174. If the noise threshold value does not fall within the point range, then the next point is examined. If the noise threshold value cannot be found to fall within any point range up to the curve peak point, then the range value is increased and the point comparisons are repeated until the noise threshold value falls within a point range which is the closest data point to the noise threshold value. These steps of the routine are illustrated by decision block 176 and by block 178. At the conclusion of this routine, the computer 92 returns the computational flow to block 110 of FIG. 3, as illustrated by return block 180.

The routine of FIG. 9 is repeated for the portion of the descending curve to find the point at which the curve drops back below the noise threshold. In this routine, however, the curve data point index "n" of block 168 is set to the peak point index value; the "n" index comparison of decision block 176 is made to the last point index value rather than to the peak point index value; and the value of the actual time, in seconds, from the noise threshold point, is indicated by the value "THRTIMDN." The time from the point at which the curve exceeds the noise threshold to the time of the peak of the curve, or "TIM2PEAK," is calculated by the computer 92 by taking the difference between the time at which the curve exceeds the noise threshold and the time of the peak of the curve. The time of appearance of the ultrasonically reflective contrast agent 55 in the contrast agent chamber 48 is also determined by taking the time interval difference between the points where the curve crosses the ascending and descending noise threshold points, ascending and descending noise threshold points, i.e., THRTIMUP−THRTIMDN−=time of appearance.

Figure 10:
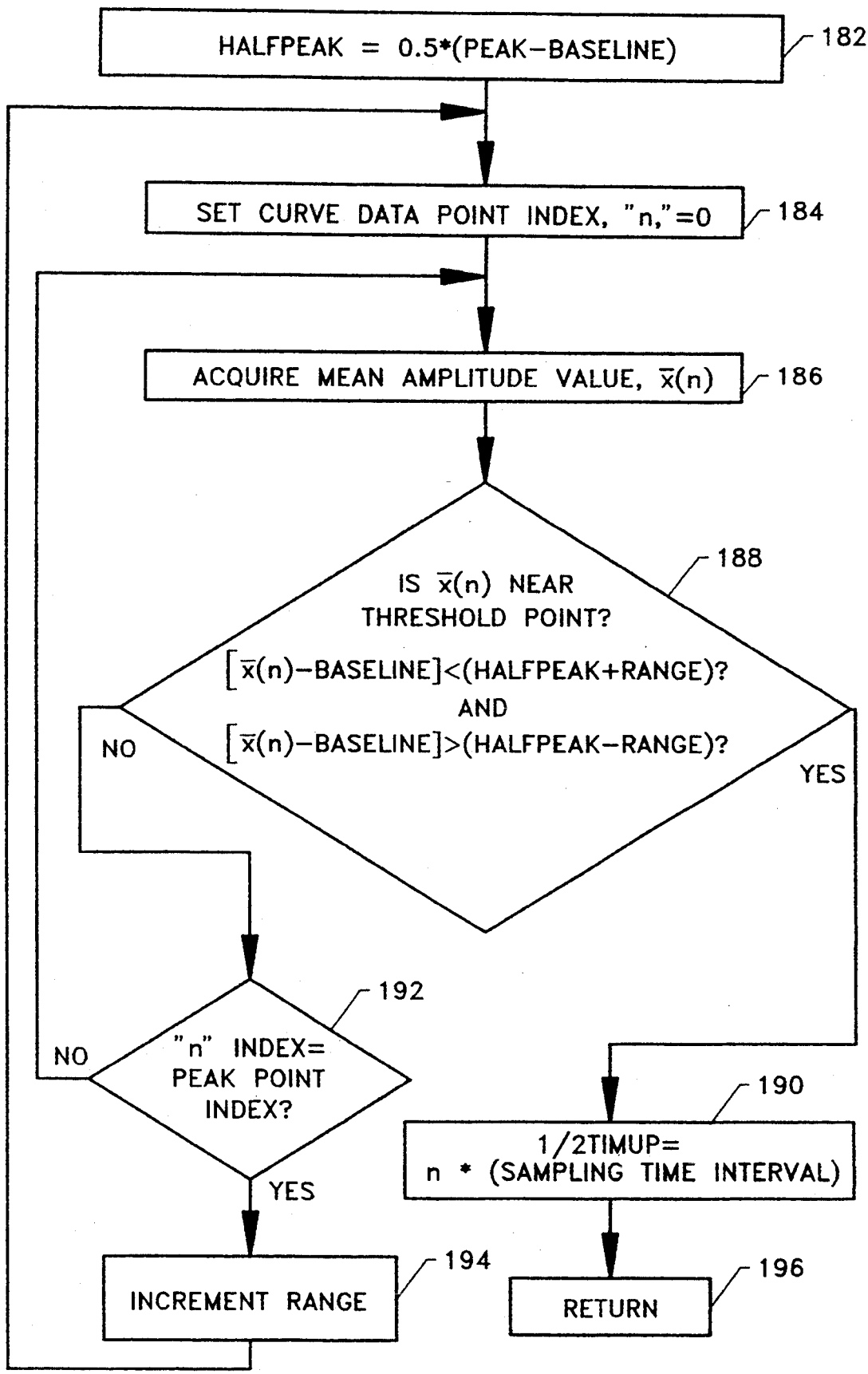
FIG. 10 is a flow diagram of the routine for calculating the time interval from the noise threshold point to the amplitude point halfway between the noise threshold point and the curve peak point for the ascending portion of the curve.

FIG. 10 illustrates the routine for calculating the time interval from the noise threshold point to the amplitude point halfway between the noise threshold point and the curve peak point for the ascending portion of the curve. What is desired is the time index of the mean amplitude value closest to the half-time ascending and half-time descending amplitude values. The routine operates by first determining the half-peak value, described as "HALFPEAK" in block 182, by multiplying the difference between the peak and baseline valves by 0.5. The next step, illustrated in block 184, is to set the curve data point index, "n," to zero. A mean amplitude data point is acquired from the memory of the computer 92, as illustrated by block 186, and a comparison is made in decision block 188 to determine if the mean amplitude data point is near the threshold point. If the half-time value is within a range of each data point value plus or minus a prescribed range value, then that is the half-time point value. To determine the actual half-time value in seconds, the time index of the mean amplitude data point within the point range is multiplied by the sampling time interval to yield the value "½TIMUP," as illustrated by block 190.

If the half-time value does not fall within that point range, then the next point is examined. If it cannot be found to fall within any point range up to the curve peak point, then the range value is incremented and the point comparisons repeated until the half-time value falls within a point range which is the closest data point to the half-time value. These steps of the routine are illustrated by blocks 192 and 194. At the conclusion of this routine, the computer 92 returns the computational flow to block 110 of FIG. 3, as illustrated by the return block 196.

The routine of FIG. 10 is repeated for the portion of the descending curve. In this routine, however, the curve data point index "n" of block 184 is set to the peak point index value; the "n" index comparison of decision block 192 is made to the last point index value rather than to the peak point index value; and the value of the actual time, in seconds, in indicated by the value "½TIMDN."

The slope of the curve at the half-time ascending and descending points is calculated by the computer 92 by taking the difference between two bracketing time related points and dividing by the number of points between the values. Then dividing by the time interval between each point gives the slope in amplitude units per second. The formulas for the slopes are:

1/2 TIMUP SLOPE =

$$\frac{x(1/2 \text{ TIMUP INDEX} + \text{INDEX SPREAD}) - x(1/2 \text{ TIMUP INDEX})}{(\text{INDEX SPREAD}) \cdot (\text{SAMPLING TIME VALUE})}$$

and

1/2 TIMDN SLOPE =

$$\frac{x(1/2 \text{ TIMDN INDEX} + \text{INDEX SPREAD}) - x(1/2 \text{ TIMDN INDEX})}{(\text{INDEX SPREAD}) \cdot (\text{SAMPLING TIME VALUE})}$$

Figure 11:
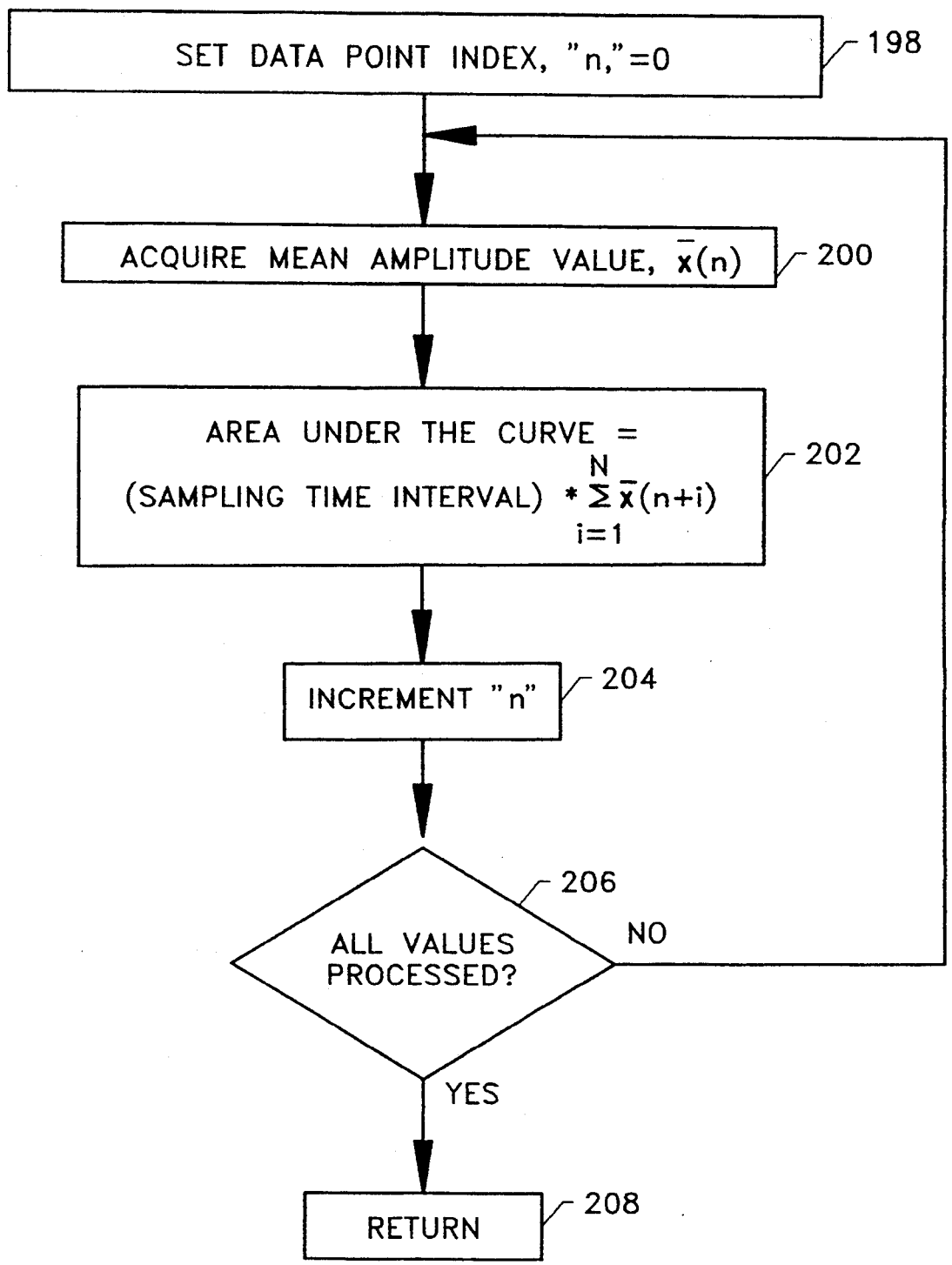
FIG. 11 is a flow diagram of the routine for calculating the area under the mean amplitude data points against time curve.

FIG. 11 illustrates the routine to calculate the area under mean amplitude data points against time curve. A typical curve is depicted in FIG. 12. The area is computed by multiplying each amplitude point by the time interval between the points and summing the result. The routine begins at block 198 by setting the data point index "n" to zero. A mean amplitude data point is acquired from the memory of the computer 92, as illustrated by block 200, and the area under the curve is calculated, as depicted by block 202. The value of "n" is incremented, as depicted in block 204, and processing continues until all of the mean amplitude values are processed, as indicated by decision block 206. The computer 92 then returns the computational flow to block 110 of FIG. 3 as indicated by return block 208.

I claim:

1. A method of characterizing the time and frequency response of an ultrasonically reflective contrast agent comprising the steps of:
    injecting, under constant pressure, an ultrasonically reflective contrast agent into a fluid stream;
    passing the fluid stream through a mixing chamber to uniformly mix the ultrasonically reflective contrast agent and the fluid stream;
    passing the uniform mixture of the ultrasonically reflective contrast agent and the fluid stream through a contrast agent chamber;
    transmitting a pulse of ultrasonic energy into the contrast agent chamber;
    receiving an echo waveform from the ultrasonically reflective contrast agent; and
    analyzing the echo waveform to determine the time and frequency response of the ultrasonically reflective contrast agent.

2. The method of claim 1 wherein the pulse of ultrasonic energy is in the radio frequency range.

3. The method of claim 1 wherein the step of analyzing the echo waveform comprises the steps of:
    digitizing the echo waveform into discrete data points;
    computing mean amplitude data points from the discrete data points;
    correcting spurious mean amplitude data points;
    smoothing the mean amplitude data points;
    plotting the mean amplitude data points against time; and
    performing parameter calculations on the plot of the mean amplitude data points against time curve.

4. The method of claim 3 wherein the step of computing mean amplitude data points from the discrete data points comprises the steps of:
    acquiring a number of discrete data points;
    averaging the absolute value of the discrete data points to obtain a mean amplitude data point;
    storing the mean amplitude data point under a time index address;
    incrementing the time index address; and
    repeating the acquiring, averaging, storing, and incrementing steps until the uniform mixture of fluid and ultrasonically reflective contrast agent has passed out of the contrast agent chamber.

5. The method of claim 4 wherein the step of correcting spurious mean amplitude data points comprises the steps of:
    computing first a running average of a number of mean amplitude data points;
    comparing each mean amplitude data point to the first running average to determine if the point is outside the first running average plus or minus a range value; and
    correcting each mean amplitude data point that is outside of the first running average plus or minus a range value by substituting the first running average for that point.

6. The method of claim 5 wherein the step of smoothing the mean amplitude data points comprises the steps of:
    computing a second running average of a number of mean amplitude data points; and
    substituting the second running average for each mean amplitude data point.

7. A method of characterizing the time and frequency response of an ultrasonically reflective contrast agent comprising the steps of:
    injecting, under constant pressure, an ultrasonically reflective contrast agent into a fluid flowing through a pump flow circuit;
    passing the fluid through a mixing chamber to uniformly mix the ultrasonically reflective contrast agent and the fluid;
    passing the uniform mixture of the ultrasonically reflective contrast agent and the fluid through a contrast agent chamber that is acoustically interposed between an acoustic isolation chamber and an ultrasonic transducer chamber;
    transmitting a pulse of ultrasonic energy into the contrast agent chamber;
    receiving an echo waveform from the ultrasonically reflective contrast agent; and
    analyzing the echo waveform to determine the time and frequency response of the ultrasonically reflective contrast agent.

8. The method of claim 7 wherein the fluid is selected from the group consisting of water and saline.

9. Apparatus for analyzing an ultrasonically reflective contrast agent comprising:
    a pump flow circuit;
    a fluid flowing through said pump flow circuit;
    means for injecting, under constant pressure, an ultrasonically reflective contrast agent into the first fluid;
    means for uniformly mixing the fluid and the ultrasonically reflective contrast agent;
    a contrast agent chamber adapted for receiving the uniform mixture of the fluid and the ultrasonically reflective contrast agent;
    ultrasonic transducer means for transmitting a pulse of ultrasonic energy into the contrast agent chamber and for receiving an echo waveform from the ultrasonically reflective contrast agent; and
    means for analyzing the echo waveform to determine the time and frequency response of the ultrasonically reflective contrast agent.

10. The apparatus of claim 9 wherein the fluid is selected from the group consisting of water and saline.

11. The apparatus of claim 9 wherein said means for injecting, under constant pressure, an ultrasonically reflective contrast agent comprises:
    a tube;
    a syringe containing the ultrasonically reflective contrast agent and having a plunger;
    a weight;
    wherein the syringe and the weight are disposed within the tube; and
    trigger means for supporting and releasing the weight such that the weight presses against the plunger of the syringe with a constant force to cause the ultrasonically reflective contrast agent to be injected into the fluid under constant pressure.

12. The apparatus of claim 9 wherein said means for uniformly mixing the fluid and the ultrasonically reflective contrast agent comprises a cylindrical chamber.

13. The apparatus of claim 9 wherein said contrast agent chamber comprises a cylindrical chamber having an open first side and an open second side, a first membrane seal attached to the first side, and a second membrane seal attached to the second side.

14. The apparatus of claim 13 further comprising:
a cylindrical acoustic isolation chamber having an open first side and closed second side;
a cylindrical ultrasonic transducer chamber having an open first side and an open second side;
a third seal;
a first liquid filling the cylindrical acoustic isolation chamber;
a second liquid filling the cylindrical ultrasonic transducer chamber;
wherein the cylindrical acoustic chamber has the same diameter as the contrast agent chamber, is adjacent to the second side of and axially aligned with the contrast agent chamber, and is sealed with the second membrane seal;
wherein the cylindrical ultrasonic transducer chamber has the same diameter as the contrast agent chamber, is adjacent to the first side of and axially aligned with the contrast chamber, and is sealed on its second side with the first membrane seal and sealed on its first side with tile third seal; and
the ultrasonic transducer means is mounted in the third seal.

15. The apparatus of claim 14 wherein the first liquid is selected from the group consisting of water and saline.

16. The apparatus of claim 14 wherein the second liquid is selected from the group consisting of water and saline.

17. A method of analyzing an ultrasonic echo waveform received from an ultrasonically reflective contrast agent comprises the steps of:
digitizing the echo waveform into discrete data points;
computing mean amplitude data points from the discrete data points;
correcting spurious mean amplitude data points;
smoothing the mean amplitude data points;
plotting the mean amplitude data points against time; and
performing parameter calculations on the plot of the mean amplitude data points against time curve.

18. The method of claim 17 wherein the step of computing mean amplitude data points from the discrete data points comprises the steps of:
acquiring a number of discrete data points;
averaging the absolute value of the discrete data points to obtain a mean amplitude data point;
storing the mean amplitude data point under a time index address;
incrementing the time index address; and
repeating the acquiring, averaging, storing, and incrementing steps until the uniform mixture of fluid and ultrasonically reflective contrast agent has passed out of the contrast agent chamber.

19. The method of claim 18 wherein the step of correcting spurious mean amplitude data points comprises the steps of:
computing first a running average of a number of mean amplitude data points;
comparing each mean amplitude data point to the first running average to determine if the point is outside the first running average plus or minus a range value; and
correcting each mean amplitude data point that is outside of the first running average plus or minus a range value by substituting the first running average for that point.

20. The method of claim 19 wherein the step of smoothing the mean amplitude data points comprises the steps of:
computing a second running average of a number of mean amplitude data points; and
substituting the second running average for each mean amplitude data point.

* * * * *